(12) United States Patent
Adams et al.

(10) Patent No.: US 6,527,784 B2
(45) Date of Patent: *Mar. 4, 2003

(54) TEXTURED LIGATING BAND AND METHOD OF USE OF SAME

(75) Inventors: Ronald David Adams, Holliston, MA (US); Michael Banik, Bolton, MA (US); Steve Moreci, Milford, MA (US)

(73) Assignee: SciMed Life Systems, Inc., Maple Grove, MN (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 09/363,094

(22) Filed: Jul. 30, 1999

(65) Prior Publication Data

US 2002/0183767 A1 Dec. 5, 2002

Related U.S. Application Data

(63) Continuation of application No. 08/866,989, filed on Jun. 2, 1997, now Pat. No. 5,976,158.

(51) Int. Cl.[7] .............................................. A61B 17/12
(52) U.S. Cl. ..................................... 606/140; 606/157
(58) Field of Search ............................... 606/140, 141, 606/157, 201; 128/831, 832, 843; 600/41

(56) References Cited

U.S. PATENT DOCUMENTS

| | | | |
|---|---|---|---|
| 1,683,119 A | 9/1928 | Ziegler | |
| 3,880,166 A | 4/1975 | Fogarty | |
| 4,416,275 A * | 11/1983 | Omley | |
| 4,485,814 A * | 12/1984 | Yoon | |
| 4,539,980 A * | 9/1985 | Chaney | |
| 4,794,927 A * | 1/1989 | Yoon | |
| 4,860,746 A | 8/1989 | Yoon | |
| 4,881,939 A | 11/1989 | Newman | |
| 4,938,765 A | 7/1990 | Rasmusson | |
| 5,074,869 A | 12/1991 | Daicoff | |
| 5,201,900 A * | 4/1993 | Nardella | 606/157 |
| 5,303,937 A * | 4/1994 | Huss et al. | 277/215 |
| 5,356,416 A * | 10/1994 | Chu et al. | 606/140 |
| 5,462,559 A | 10/1995 | Ahmed | |
| 5,507,797 A | 4/1996 | Suzuki et al. | |
| 5,578,047 A * | 11/1996 | Taylor | 606/157 |
| 5,624,453 A | 4/1997 | Ahmed | |
| 5,695,444 A * | 12/1997 | Chaney | 600/38 |
| 5,702,411 A | 12/1997 | Back et al. | |
| 5,752,966 A | 5/1998 | Chang | |
| 5,972,009 A | 10/1999 | Fortier et al. | |
| 5,976,158 A | 11/1999 | Adams et al. | |
| 5,980,537 A | 11/1999 | Ouchi | |
| 6,039,750 A * | 3/2000 | Kubalak et al. | 606/201 |

FOREIGN PATENT DOCUMENTS

| | | | |
|---|---|---|---|
| GB | 649226 | * | 1/1951 |
| GB | 1530282 | * | 10/1978 |

* cited by examiner

Primary Examiner—Michael H. Thaler
(74) Attorney, Agent, or Firm—Kenyon & Kenyon

(57) ABSTRACT

An elastic band for ligating tissue within a living body comprises an inner tissue engaging surface which, when in an operative position within the body, surrounds and directly contacts the tissue. At least a portion of the inner tissue engaging surface defines a plurality of discontinuities formed by one of projections and depressions. A method of ligating tissue within a living body using such a ligating band comprises the steps of positioning the elastic band, which has been stretched to increase the size of a central opening extending therethrough, adjacent to a portion of tissue to be ligated. The tissue to be ligated is then drawn through the central opening of the elastic band and the elastic band is released so that the size of the central opening decreases to grip the tissue received therein.

6 Claims, 14 Drawing Sheets

TEXTURED LIGATING BAND AND METHOD OF USE OF SAME

This application is a continuation of application Ser. No. 08/866,989 filed Jun. 2, 1997, now U.S. Pat. No. 5,976,158.

FIELD OF THE INVENTION

The invention relates generally to the field of tissue ligation, and more particularly to an improved ligating band and a method of use of the ligating band to ligate tissue.

BACKGROUND OF THE INVENTION

Physicians have used elastic ligating bands to treat lesions, including internal hemorrhoids and mucositis and for performing mechanical hemostasis.

The object of ligation is to position a ligating band over the targeted lesion or blood vessel section by stretching the band beyond its undeformed diameter drawing the tissue to be ligated within the band and then releasing the band so that it contracts, applying inward pressure on the section of tissue caught within the band. The effect of the inward pressure applied by the band is to stop all circulation through the targeted tissue, thereby causing the tissue to die. The body then sloughs off the dead tissue or the dead tissue may be aspirated into an endoscope or a similar device.

U.S. Pat. No. 5,356,416 to Chu et al. and U.S. Pat. No. 5,398,844 to Zaslavsky et al., both of which are incorporated herein by reference, describe ligating band dispensing devices including cylindrical support surfaces over which elastic ligating bands are stretched. The cylindrical support surfaces are typically attached to the distal end of an endoscope which is advanced into the body to a target area. A user then applies suction through the endoscope to draw the tissue to be ligated into the cylindrical support surface and then releases a ligating band to contract around the tissue.

There are two problems inherent with the type of ligating bands typically used with the above-described devices. The first is that the bands have a tendency to slip off the targeted tissue before the tissue is completely ligated. One reason why a ligating band may slip off targeted tissue is because tissue contained within a ligating band is effectively "pinched" by the ligating band, creating an outward pressure on the band. Specifically, the bulb-shaped projection of tissue which has been drawn under suction into the lumen of a cylindrical support surface is pulled away from the surrounding tissue creating tension within the projection which draws the tissue of the projection back toward the its natural position. Thus, the tissue is urged to slip out of the ligating band as the band contracts. In addition, blood and fluid within the body can make the surface of the targeted tissue slick, thereby decreasing the coefficient of friction between the ligating band and the targeted tissue. Also, if the targeted tissue is an active blood vessel the "pulsing" effect of blood moving through the vessel can cause the ligating band to slip off of the targeted tissue.

A second problem with current ligating bands is that the bands are not adjustable once they have been dispensed from the ligating band dispenser. Therefore, if a band is improperly placed around a section of tissue, or if the physician placing the ligating band should wish to draw more tissue within the band, there is no effective way to adjust the band.

SUMMARY OF THE INVENTION

The present invention is directed to an elastic band for ligating tissue within a living body comprising an inner tissue engaging surface which, when in an operative position within the body, surrounds and directly contacts the tissue. At least a portion of the inner tissue engaging surface defines a plurality of discontinuities formed by one of projections and depressions. A method of ligating tissue within a living body using such a ligating band comprises the steps of positioning the elastic band, which has been stretched to increase the size of a central opening extending therethrough, adjacent to a portion of tissue to be ligated. The tissue to be ligated is then drawn through the central opening of the elastic band and the elastic band is released so that the size of the central opening decreases to grip the tissue received therein.

BRIEF DESCRIPTION OF THE DRAWINGS

The invention will be more readily understood through the following detailed description, with reference to the accompanying drawings, in which.

DESCRIPTION OF THE PREFERRED EMBODIMENT

Figure 1:
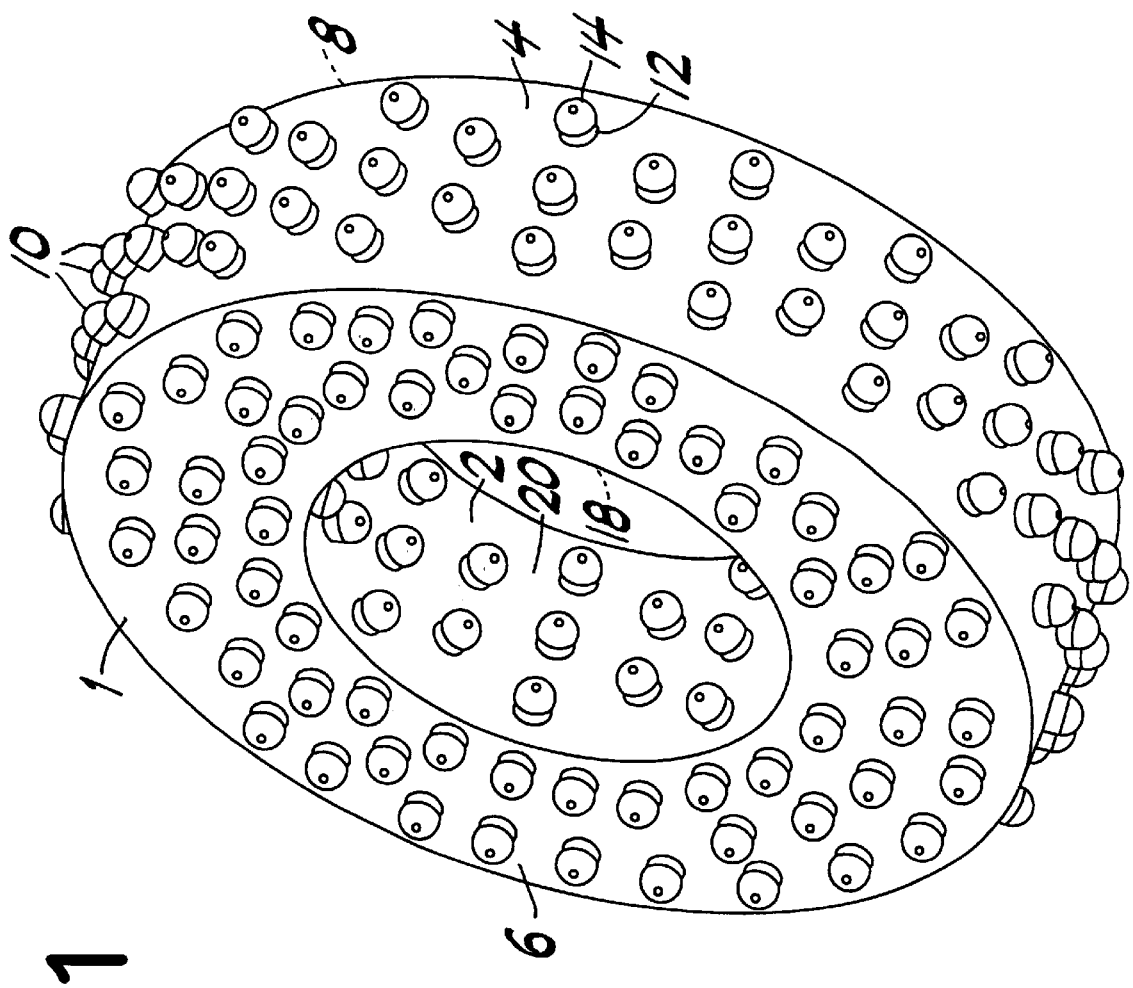
FIG. 1 is a perspective view of a first ligating band according to a embodiment of the present invention.

As illustrated in FIG. 1, a ligating band 1 is preferably formed as a ring with an inner surface 2, an outer surface 4, a first side surface 6, and a second side surface 8. Of course, those skilled in the art will understand that during manipulation, the ligating band 1 may be intentionally or accidentally twisted so that any of the surfaces 4, 6 and 8 becomes the inner surface 2. Thus, in the ligating band 1 according to the first embodiment of the invention includes texturing 10 which covers all surfaces of the ligating band 1.

The ligating band 1 according to the first embodiment has a cross-section which is substantially rectangular. That is, the ligating band 1 is formed as a portion of a cylinder. Those skilled in the art will recognize that one or more of surfaces 2, 4, 6, or 8 may be rounded reducing the distinction between the various surfaces. However, this distinction between the various surfaces is unimportant so long as the surface of the ligating band 1 which is in contact with the tissue to be ligated includes texturing as described herein.

Figure 4:
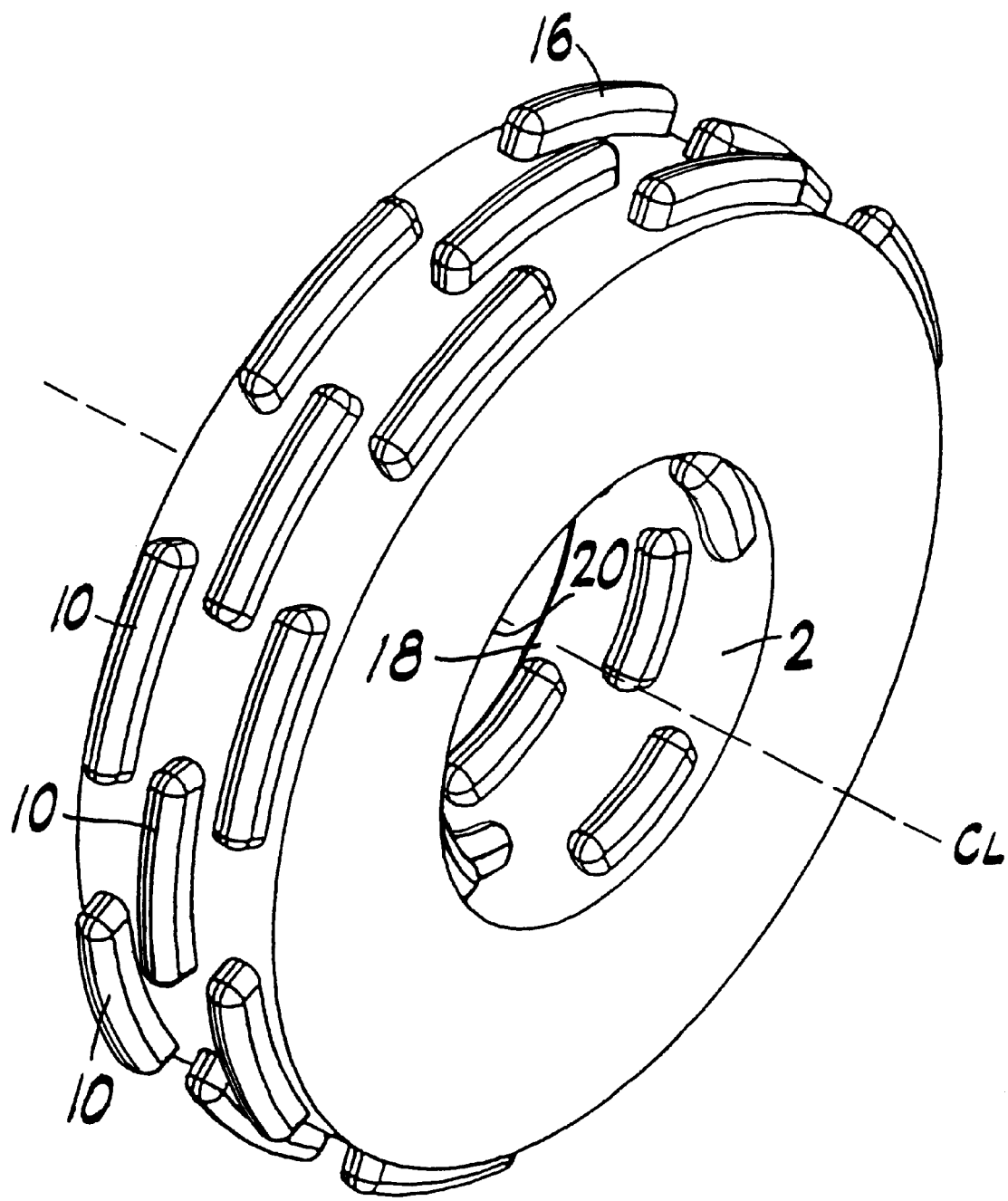
FIG. 4 is a perspective view of a ligating band according to the second embodiment of the present invention, wherein the texturing is perpendicular to the band's centerline axis.
Figure 9:
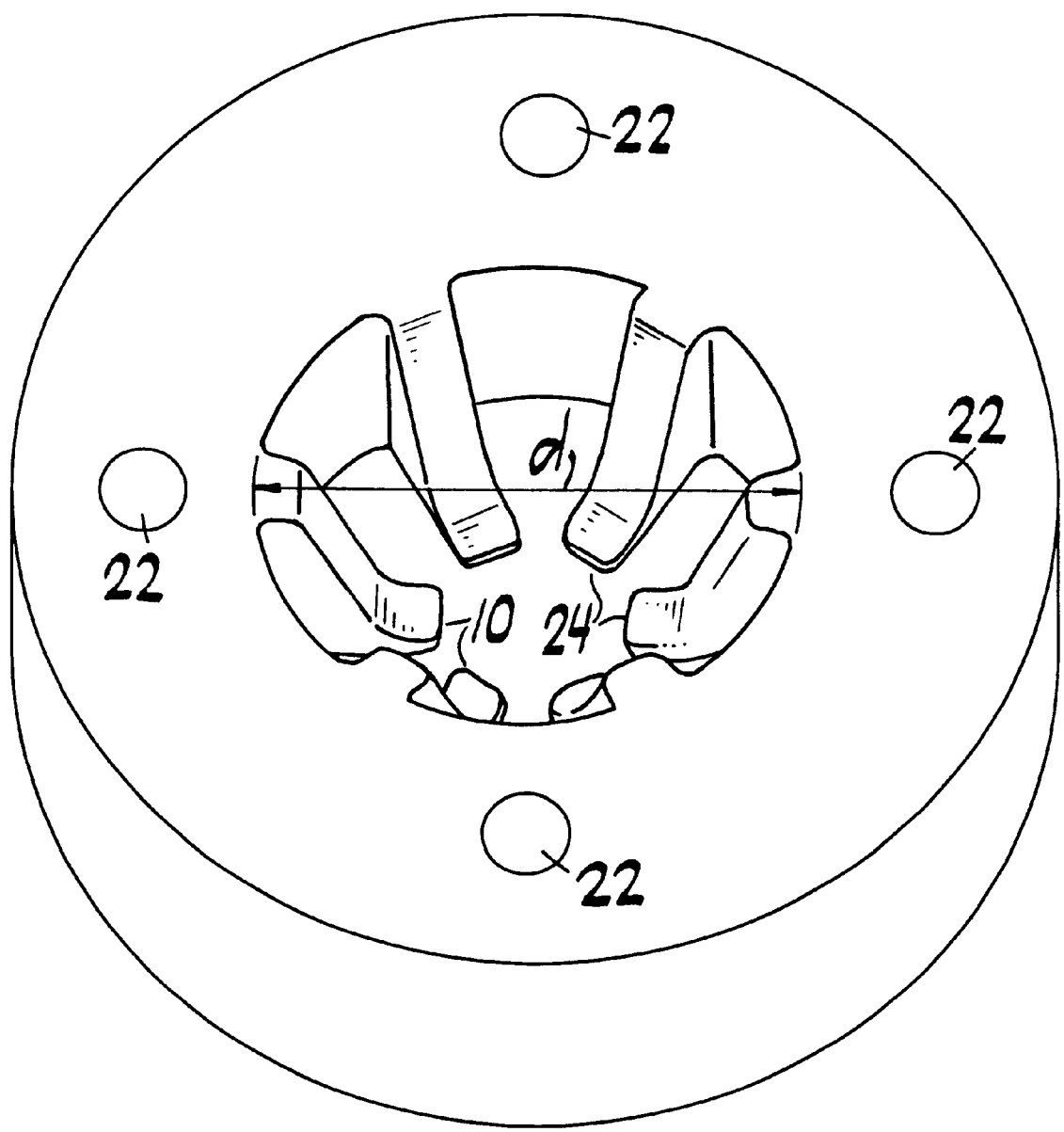
FIG. 9 is a perspective view of an alternate embodiment of the ligating band depicted in FIG. 3, wherein the texturing is comprised of securing prongs, and showing manipulating apertures.

As shown in FIG. 1, the texturing 10 is comprised of a pattern of raised bumps which are formed as cylindrical stems 12 and hemispherical caps 14. Alternate forms of texturing 10 can employ one or more of a variety of different shapes, including raised elongated members 16 as shown in FIG. 4, securing prongs 24 as shown in FIG. 9, or indentations (not shown) in the inner surface 2 of the ligating band 1. On any surface 2, 4, 6 or 8 to which the texturing 10 is applied, the texturing 10 is preferably evenly distributed.

The texturing 10 may preferably be applied to the ligating band 1 via a molding process, thereby making the texturing 10 an integral part of the structure of the ligating band 1. Preferably, the texturing 10 and the ligating band 1 are formed from latex or a synthetic equivalent thereof, such as polyisoprene. The ID (inner diameter) of the ligating bands 1 may preferably be between 0.06 and 0.10 inches and is more preferably approximately 0.07 inches. The OD (outer diameter) of the ligating bands is preferably between 0.20 and 0.24 inches, while the bands may preferably be approximately 0.08 inches thick in a direction substantially parallel to a central axis of the ligating bands 1. Of course, those skilled in the art will recognize that such a ligating band may easily be twisted so that the ID surface becomes the OD surface, etc. and that it may therefore be preferable to make the thickness of the band in each direction between 0.06 to 0.18 inches.

The texturing 10 is applied to the ligating band 1 so that the raised bumps on a first side 18 of the inner surface 2 and the raised bumps on a second side 20 thereof combine to form an interlocking pattern. By interlocking those skilled in the art will understand that the raised bumps on both the first side 18 and the second side 20 hold the tissue to be ligated by the ligating band 1 more securely in place when the ligating band 1 applies inward pressure on said tissue with the bumps from one side forcing the tissue into a gap between the bumps on the other side. Thus, as shown in FIG. 4, raised elongated members 16 on the first side 18 of the inner surface 2 may also form an interlocking pattern with respect to the second side 20 of the inner surface 2.

Figure 8:
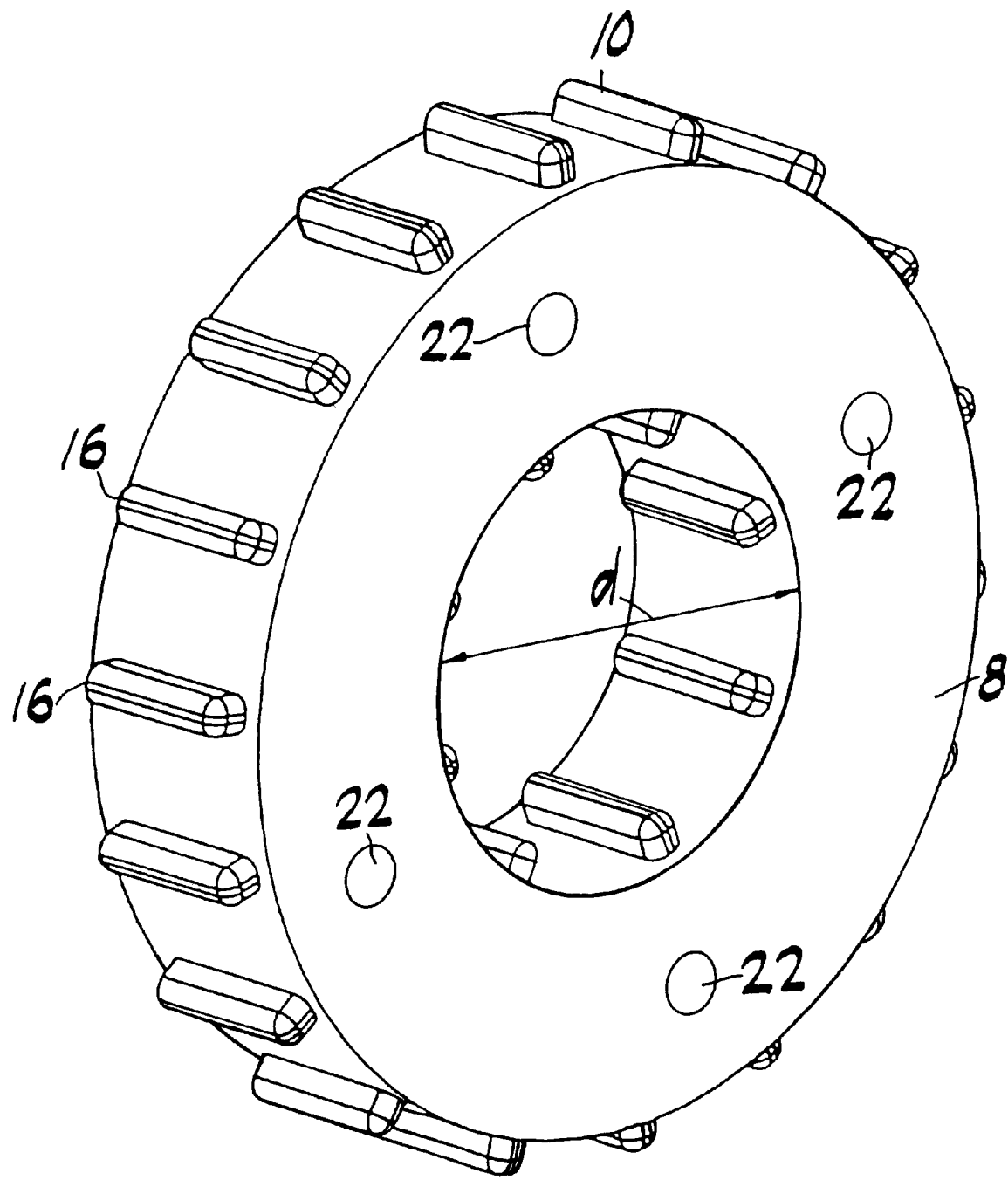
FIG. 8 is a perspective view of an alternate embodiment of the ligating band depicted in FIG. 2, wherein the texturing is parallel to the band's centerline axis, and showing manipulation apertures.

As shown in FIG. 8, an ligating band 1 according to the present invention may also include one or more manipulating apertures 22. If manipulating apertures 22 are used in conjunction with an ligating band 1, it is preferable to have at least three manipulating apertures 22 but, may have four or more. The purpose of the manipulating apertures 22 is to allow the physician placing the ligating band of the present invention to control the proper placement of the ligating band on the tissue to be ligated by inserting tines 42 of a ligating band spreader 38 into the apertures 22 and, by spreading the tines 42 apart, increasing the interior diameter d of the ligating band 1 so that the position of the ligating band 1 on the tissue to be ligated may be adjusted to allow an additional amount of tissue to be drawn up through the interior diameter d of the ligating band 1. Alternatively, the physician may use such a manipulating instrument 38 with an ligating band 1 including apertures 22 to originally place ligating bands on tissue to be ligated. That is, the physician may place an ligating band 1 including apertures 22 on the manipulating device, spread the tines 42 to increase the diameter d and manually draw tissue through the central opening in the ligating band 1. The physician may then release the ligating band 1 to ligate the tissue.

Figure 2:
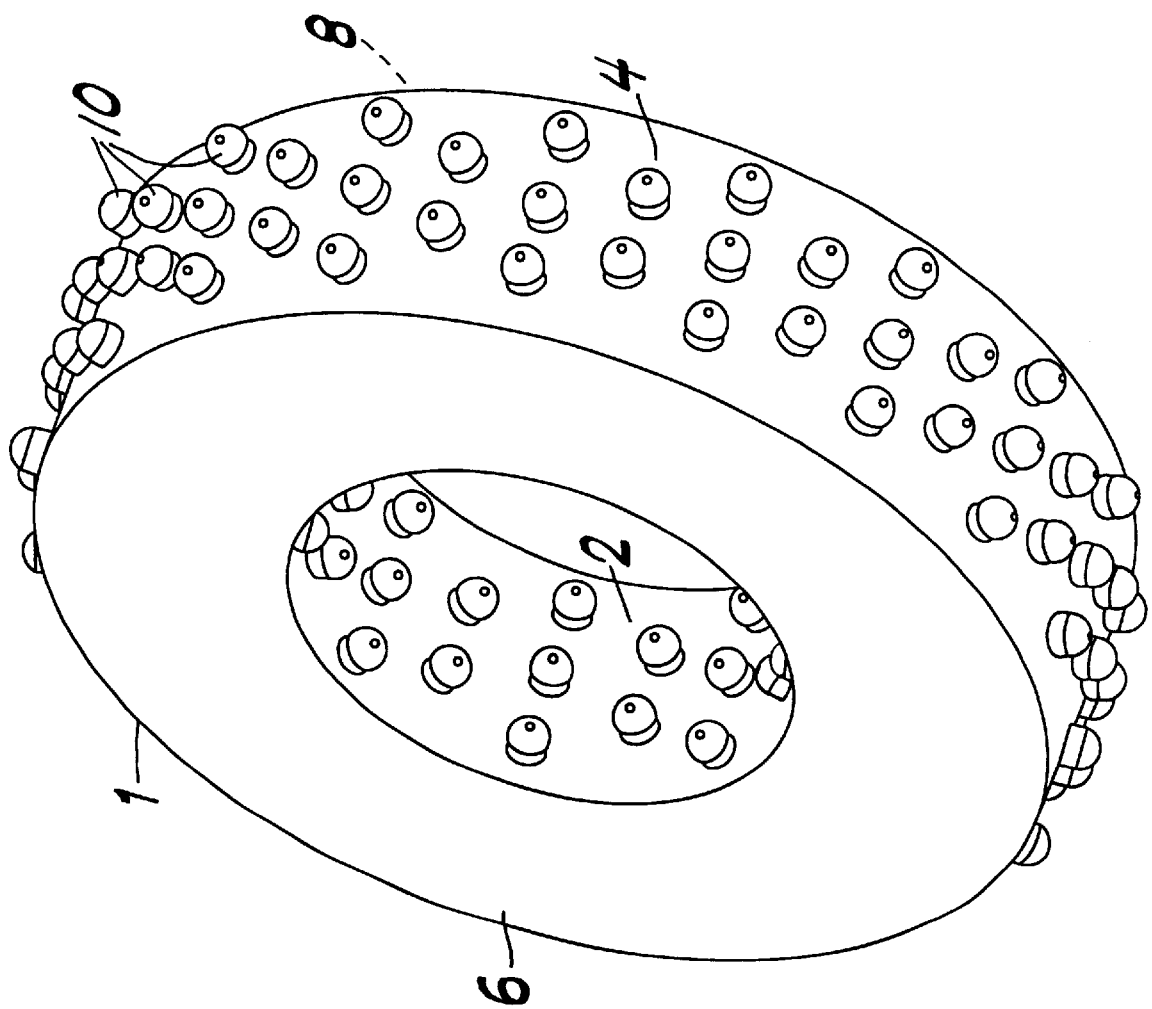
FIG. 2 is a perspective view of a ligating band according to a second embodiment of the present invention.
Figure 3:
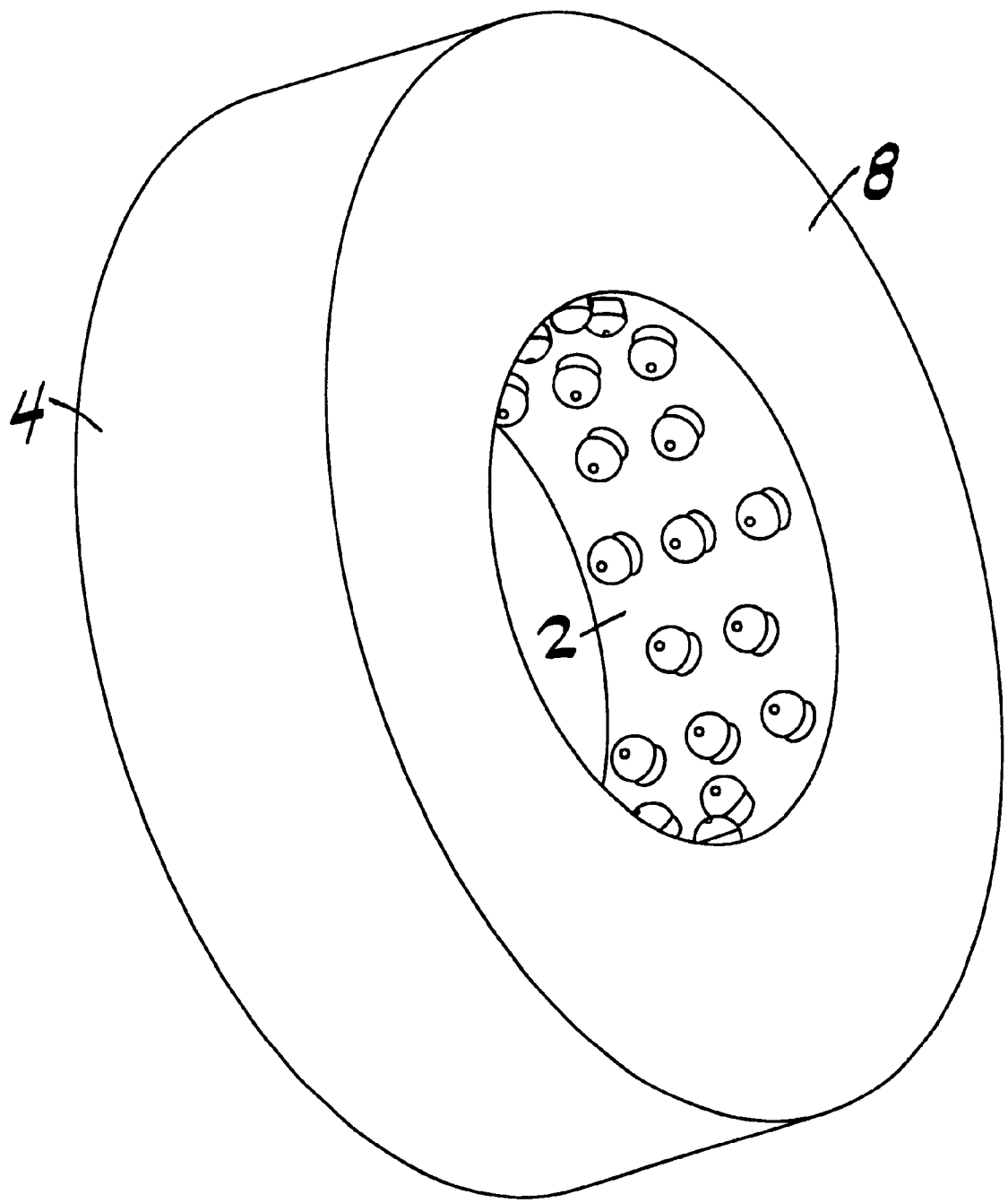
FIG. 3 is a perspective view of a ligating band according to a third embodiment of the present invention.

With reference to FIG. 1, although it is preferable to have texturing 10 on all surfaces 2, 4, 6 and 8 of the ligating band 1, it is not necessarily required so long as the user ensures that the surface including the texturing 10 remains, through the placement procedure, positioned so that it contacts the surface to be ligated. In use, the tissue to be ligated is drawn up within the interior diameter d of the ligating band 1. Thus, only texturing 10 placed on the surface positioned at inner surface 2 is designed to come in contact with the tissue to be ligated. FIG. 2 depicts an ligating band 1 according to the present invention wherein texturing 10 is provided only on the inner surface 2 and the outer surface 4, while FIG. 3 depicts an ligating band 1 according to the present invention wherein texturing 10 is provided only on the inner surface 2.

However, it is preferred that texturing 10 be provided on each of surfaces 4, 6 and 8 in addition to inner surface 2 as the ligating band 1 may "roll" after during the dispensing procedure or after being dispensed onto the tissue to be ligated. Thus, a physician cannot be certain that the ligating band 1 will not ultimately be turned "inside out" on the tissue to be ligated such that outer surface 4, for example, comes in contact with the tissue to be ligated rather than the inner surface 2.

Figure 5:
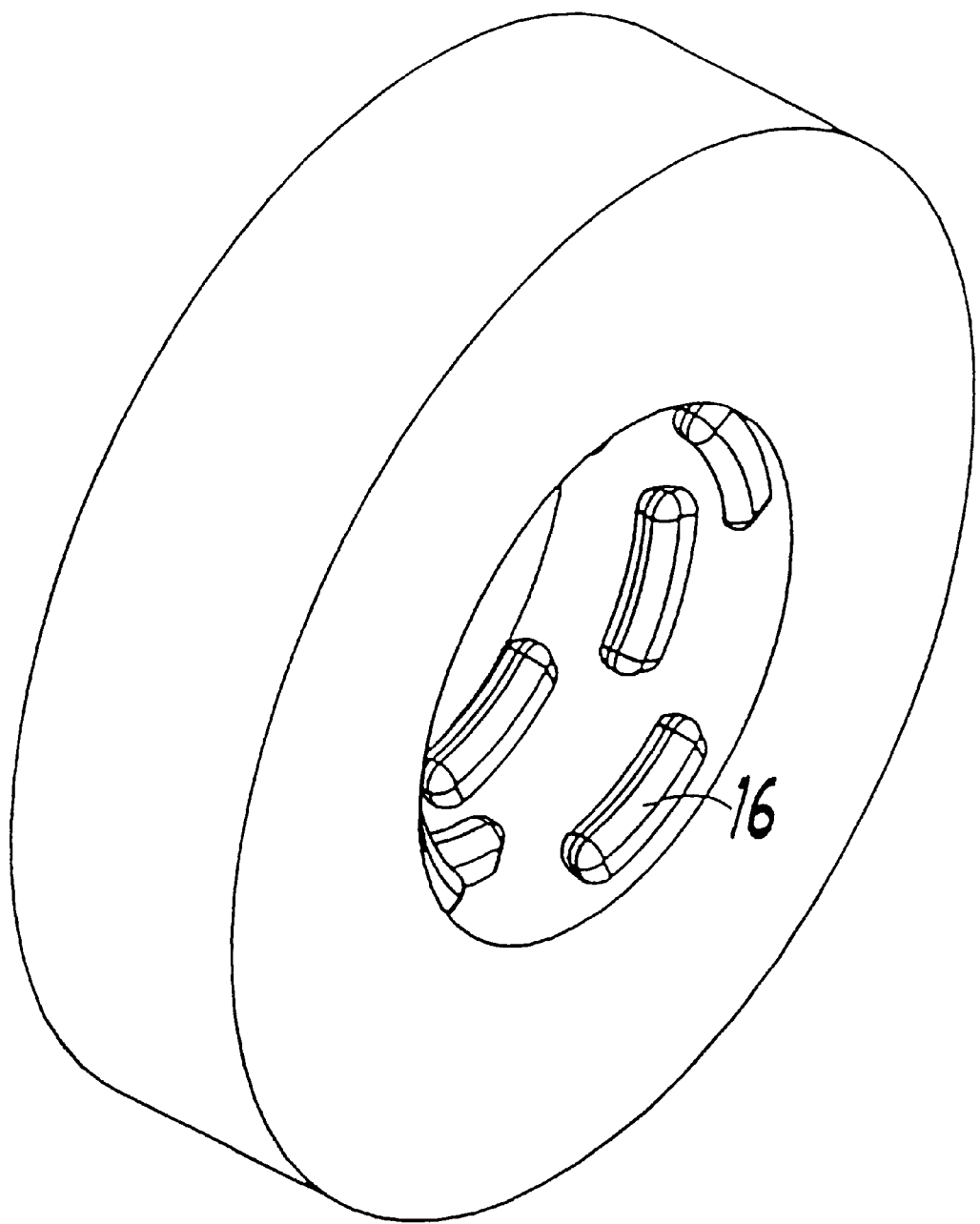
FIG. 5 is a perspective view of a ligating band according to the third embodiment of the present invention, wherein the texturing is perpendicular to the band's centerline axis.
Figure 6:
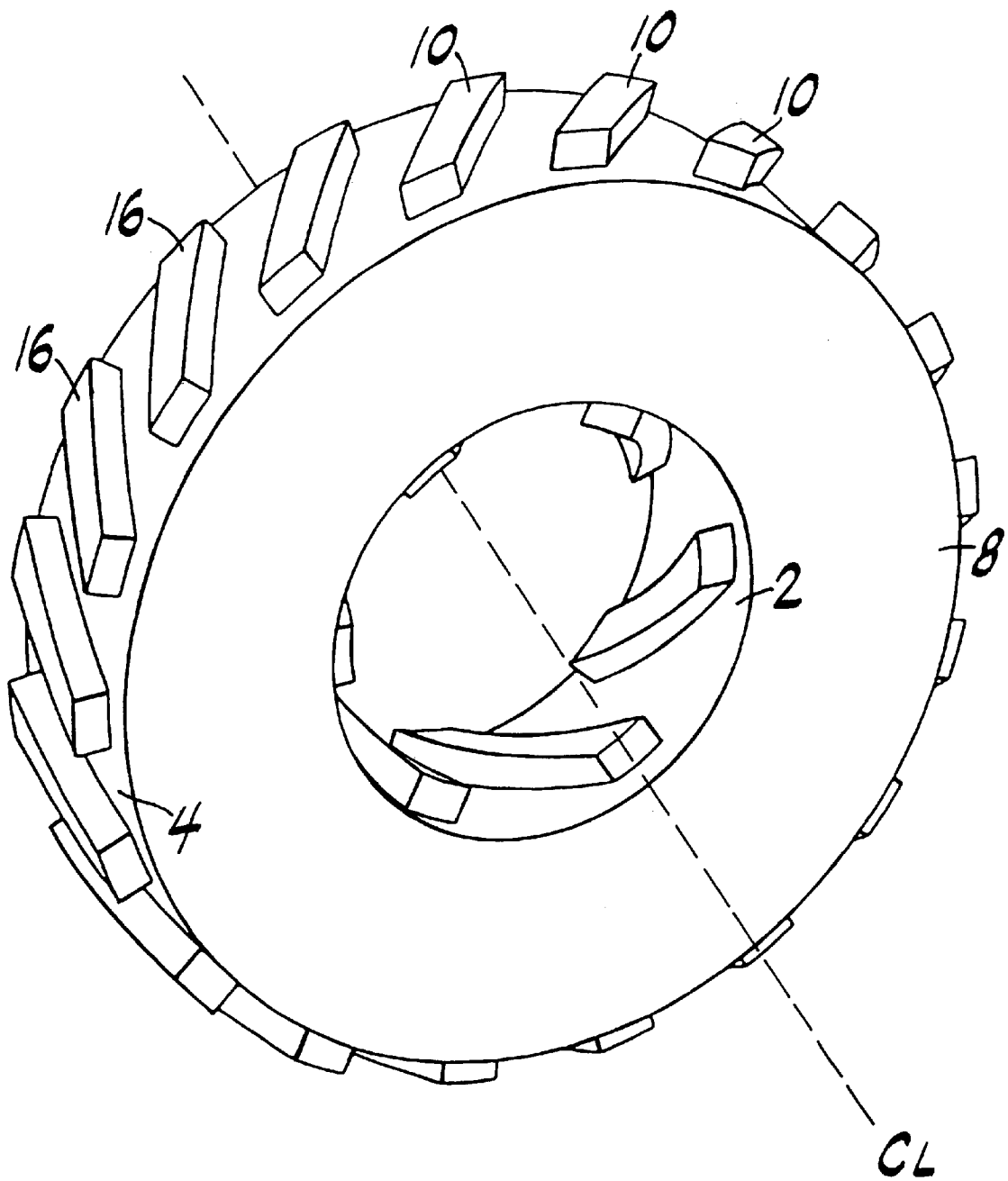
FIG. 6 is a perspective view of a ligating band according to the second embodiment of the present invention, wherein the texturing is angled to the band's centerline axis.
Figure 7:
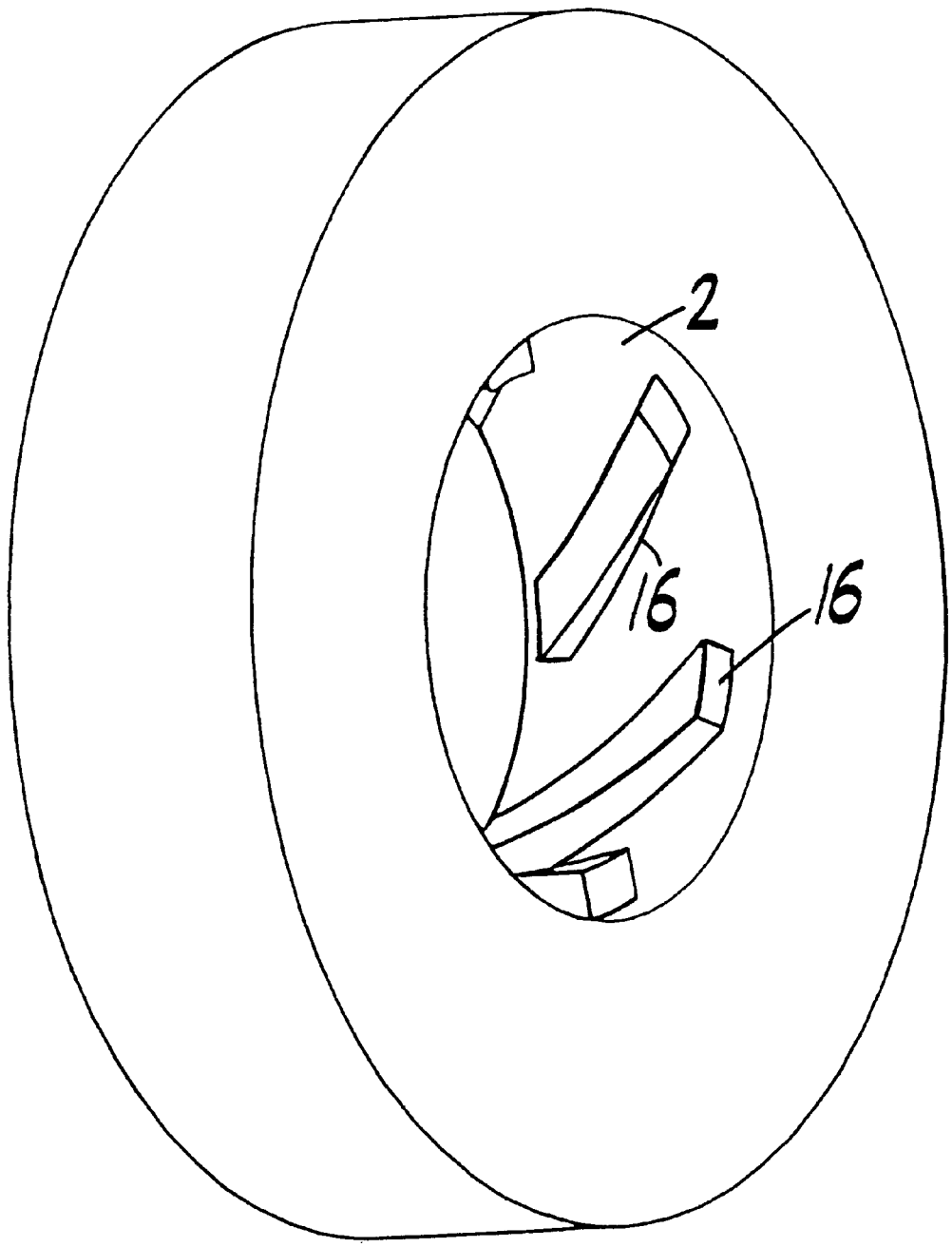
FIG. 7 is a perspective view of a ligating band according to the third embodiment of the ligating band depicted in FIG. 3, wherein the texturing is angled to the band's centerline axis.

With references to FIGS. 4 and 5, the texturing 10 may be comprised of raised elongated members 16 and placed in such a manner that the raised elongated members 16 are aligned perpendicular to the longitudinal centerline Cl of the ligating band 1. Alternately, the raised elongated members 16 may be placed at an angle, preferably between 30° and 60°, to the longitudinal centerline Cl of the ligating band 1, as shown in FIGS. 6 and 7. Alternatively, the raised elongated members 16 may be placed perpendicular to the longitudinal centerline Cl of the ligating band 1, as shown in FIG. 8.

In FIG. 9, securing prongs 24 are used to provide texturing 10 to the inner surface 2 of the ligating band 1. The securing prongs 24 perform the same function as either the other types of texturing 10 previously described; that is, the securing prongs 24 increase the resistance of the ligating band 1 to any forces acting to dislodge it from the tissue to be ligated.

Figure 10:
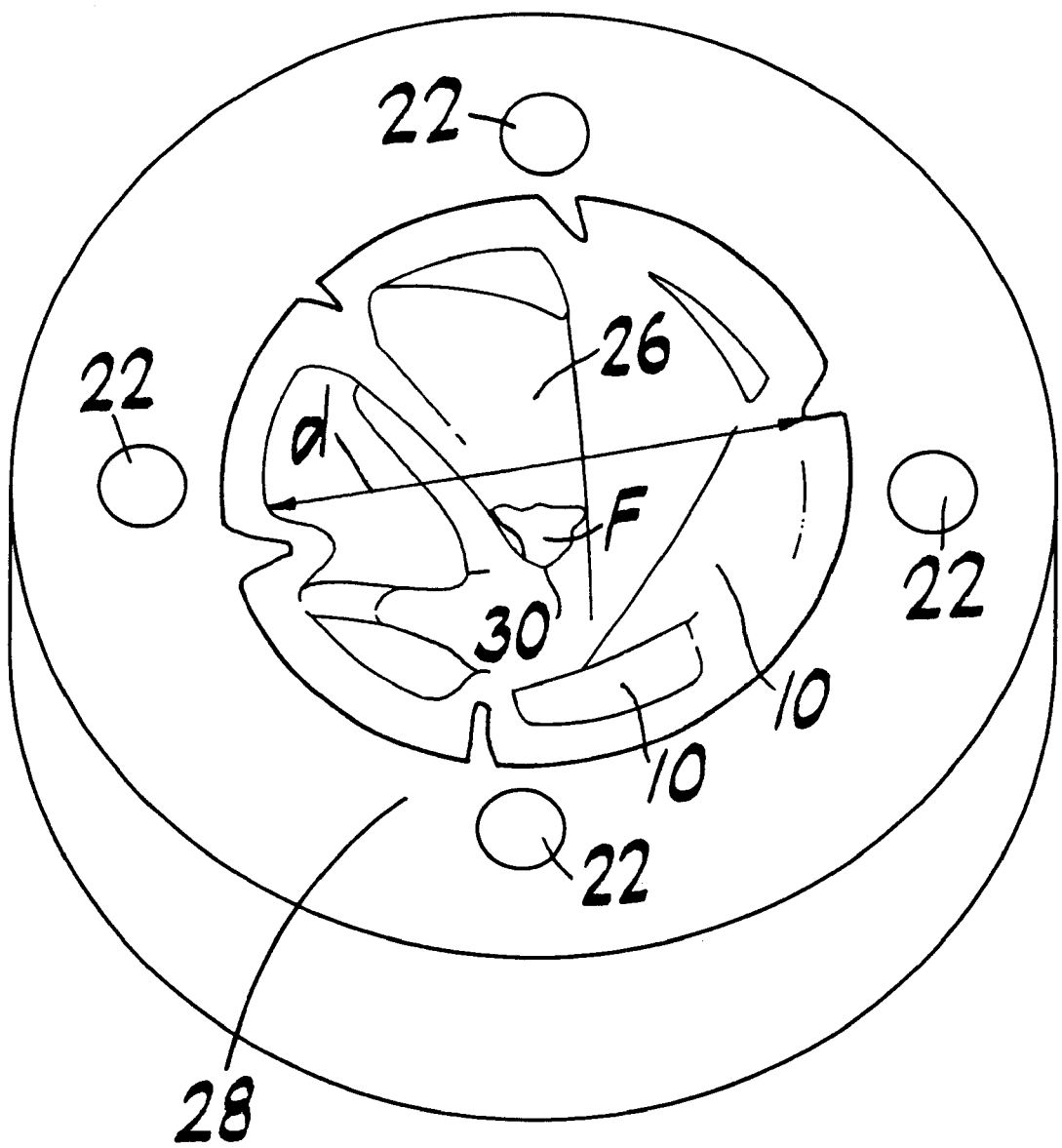
FIG. 10 is a perspective view of an alternate embodiment of the ligating band depicted in FIG. 9, wherein the securing prongs are configured as injection prongs.

The securing prongs 24 may alternately be configured as injection prongs 26, as shown in FIG. 10. After tissue to be ligated has been drawn within the interior diameter d of the ligating band 1, the ligating band 1 is allowed to return to its undeformed state, applying inward pressure on the tissue. By employing injection prongs 26, not only does the ligating band 1 depicted in FIG. 10 securely hold the tissue to be ligated in place, but it also pierces the tissue with the injection prongs 26, thereby injecting a fluid held in an interior reservoir 28 into the tissue. The fluid is injected as the return of the ligating band 1 to its undeformed state compresses the reservoir 28. Those skilled in the art will recognize that this fluid may be a sclerotherapy agent, a healing agent or any other desired medicinal fluid. Alternatively, the fluid may be coated on an area F at the tips 30 of the injection prongs 26, so that the fluid F would be injected into the tissue after the tissue to be ligated has been drawn within the interior diameter d of the ligating band 1 and the ligating band 1 has been allowed to return to its undeformed state.

Alternately, injection prongs 26 may be used to transmit RF energy into the section of tissue directly beneath the tissue to be ligated. To achieve this, the structure illustrated as the reservoir 28, is replaced by a similarly shaped and situated electrically conductive member which, after the ligating band 1 has been positioned on the tissue, may be coupled to a source of RF energy via apertures 22 to cauterize the surrounding tissue. Those skilled in the art will understand that the electrically conductive material may be in the form of a spring or other expandable shape to allow the structure to expand and contract when the ligating band is stretched or released.

In use, as shown in FIGS. 11–16, in use a physician first loads the ligating band 1 onto the distal end of a ligating band dispenser 32, such as the ligating dispenser described in U.S. Pat. No. 5,356,416, so that the interior diameter d of the ligating band 1 is substantially greater that its natural, pre-deformed interior diameter d.

Next the physician positions a distal aperture 34 of the ligating band dispenser 32 adjacent to a first section of tissue T1. The first section T1 is then drawn into the distal aperture 34, preferably under suction. Alternatively, the first section of tissue T1 may be drawn within the distal aperture 34 by mechanical means, such as a forceps, jaws, clamp, or the like (not shown). The physician then triggers the ligating band dispenser 32 to release one or more ligating bands 1 over the targeted tissue T1.

Figure 12:
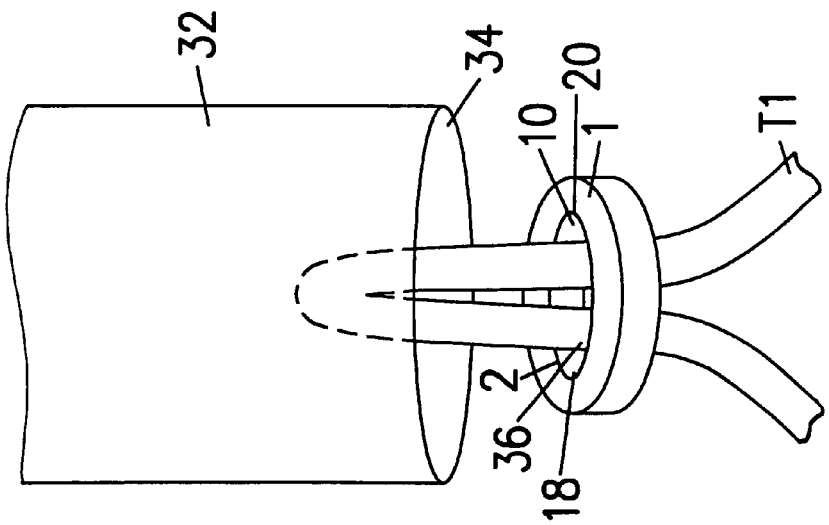
FIG. 12 shows a side view of a blood vessel with an elastic ligating band received thereon.
Figure 11:
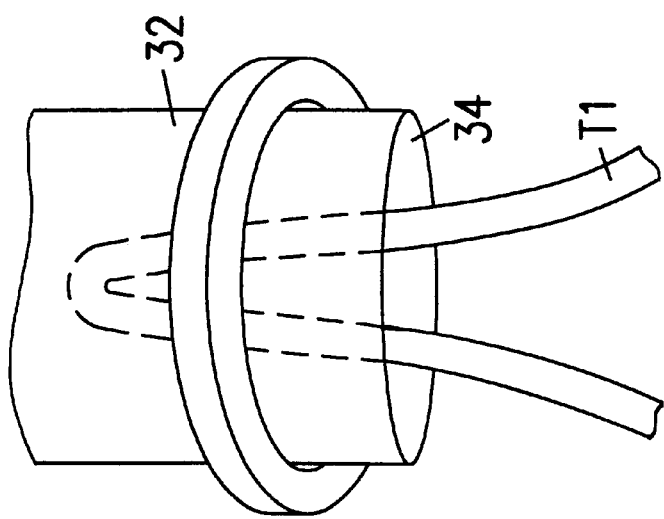
FIG. 11 shows a side view of a blood vessel drawn into a device for applying ligating bands.
Figure 14:
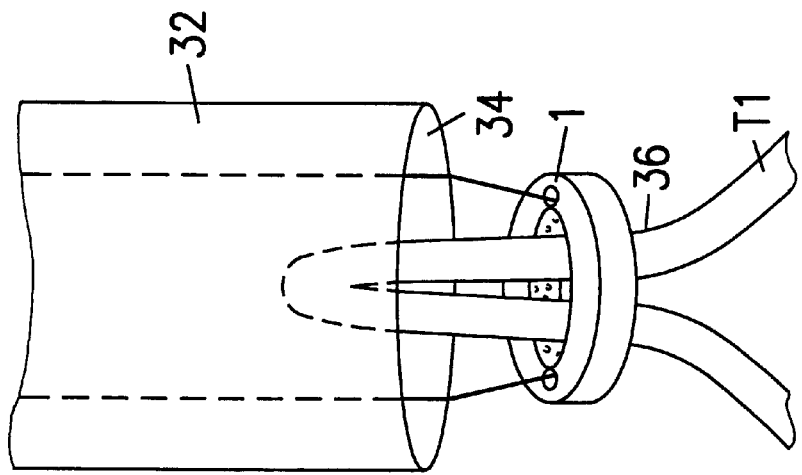
FIG. 14 shows a side view of the blood vessel of FIG. 13, wherein the elastic ligating band has been released.
Figure 13:
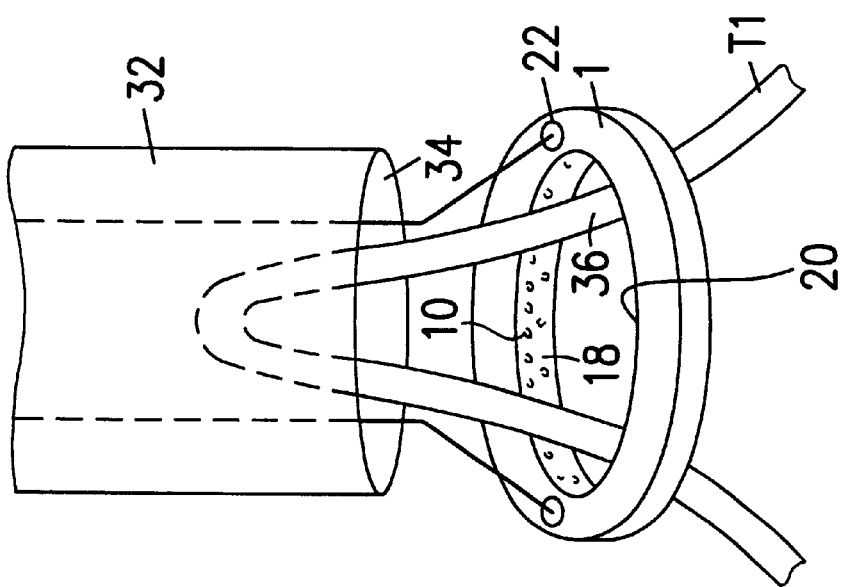
FIG. 13 shows a side view of a blood vessel received within a device for applying ligating bands wherein the elastic ligating band has been reopened on the blood vessel to adjust its position.
Figure 15:
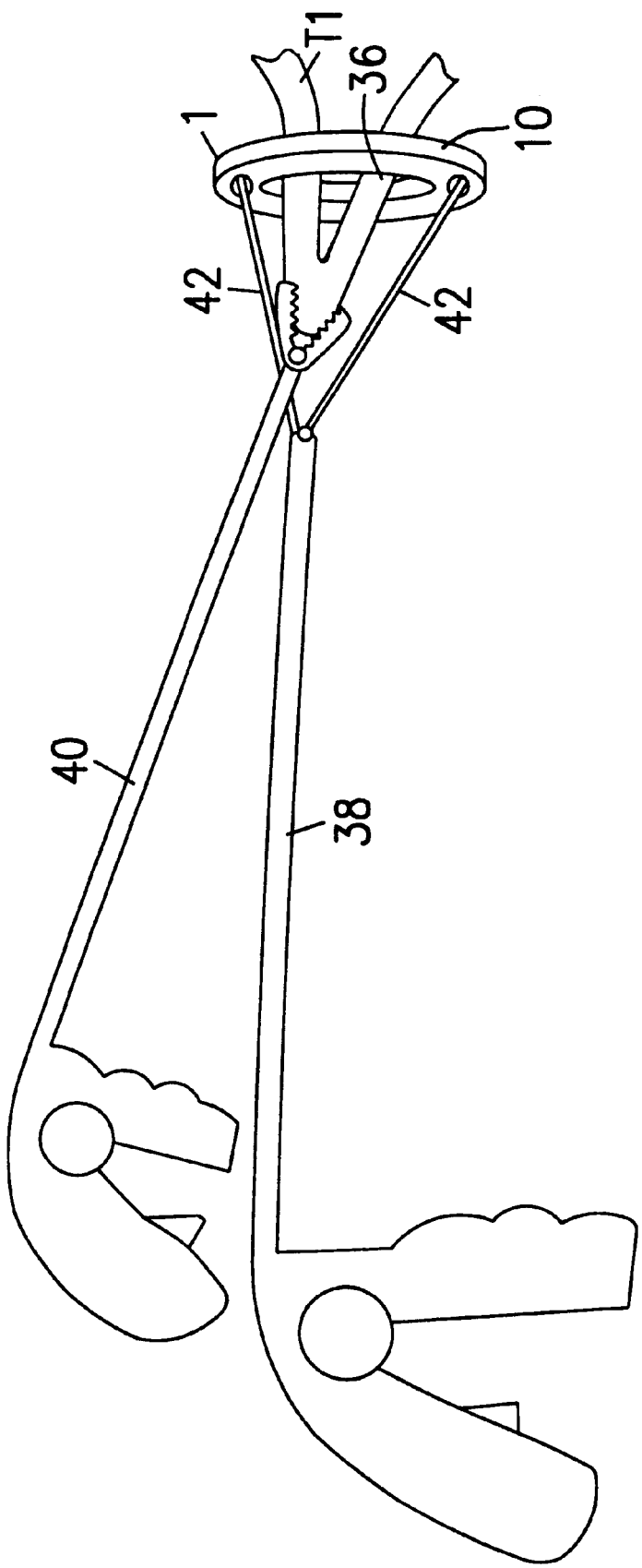
FIG. 15 shows a side view of a ligating band of FIG. 9, wherein a ligating band spreading device is being used to stretch the ligating band while a mechanical gripping device is used to draw tissue through the central opening in the ligating band.
Figure 16:
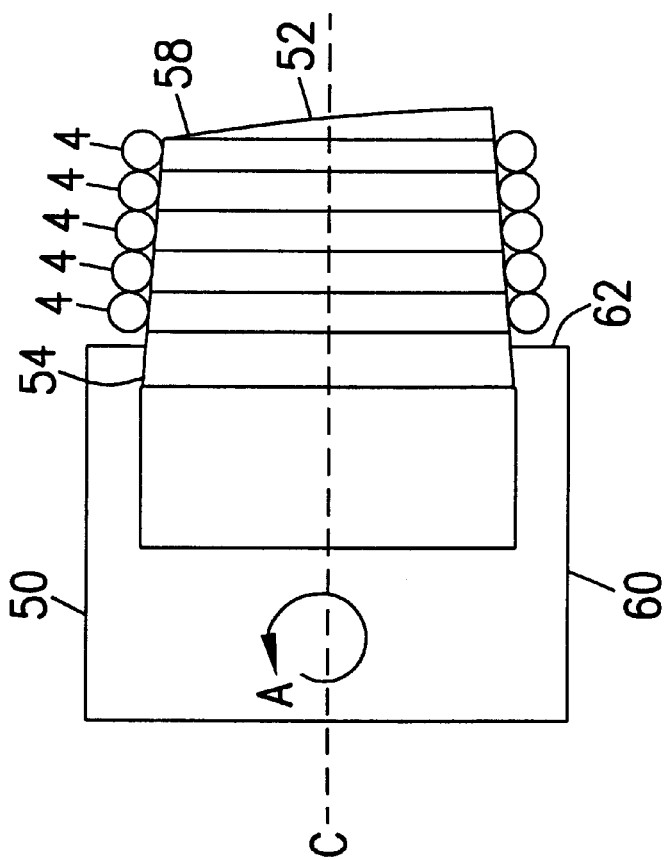
FIG. 16 shows a side view of the ligating band of FIG. 9 wherein the ligating band spreading device has been inserted through a central channel formed through an endoscope or other insertion device.

As seen in FIG. 12, when the ligating band 1 has been dispensed from the ligating band dispenser 32, the interior diameter d of the ligating band 1 suddenly decreases as the ligating band 1 seeks to return to its predeformed state. As the interior diameter d decreases, the texturing 10 on the inner surface 2 of the ligating band 1 engages a portion 36 of the first section of tissue 33 and exerts inward pressure on the tissue 36. The pressure on the tissue 39 stops all circulation through the targeted tissue T1, thereby causing the portion 36 to die. The body then sloughs off the dead tissue 36. Alternatively, the dead tissue 36 may be removed by mechanical means and aspirated into an endoscope, the ligating band dispenser 32, or a similar device.

While the texturing 10 on the inner surface 2 of the ligating band 1 is exerting inward pressure on the tissue 36, the texturing 10 restricts the movement of the ligating band 1 over the tissue 36. Thus, the ligating band 1 of the present invention is less likely than prior art ligating bands to be displaced from the targeted tissue 36 in response to outward pressures caused by the "pinching" of the targeted tissue 33 or by the movement of blood or other fluid through the targeted tissue T1. In addition, when the texturing 10 on the inner surface 2 of the ligating band 1 is exerting inward pressure on the tissue 36, it is preferable that the texturing 10 on the first side 18 of the inner surface 2 remotely engages the texturing 10 on the second side 20 of the inner surface 2 through the portion 36 of tissue to form an interlocking pattern. By forming such an interlocking pattern, the texturing 10 more effectively restricts the movement of the ligating band 1 relative to the tissue 36.

As discussed previously, the optional manipulation apertures 22 provide the physician with the ability to place the ligating band 1 directly over the targeted tissue 36 and then decrease the interior diameter d until the texturing 10 on the inner surface 2 of the ligating band 1 engages and exerts inward pressure against the tissue 36. To position the ligating band 1, the physician loads the ligating band 1 onto a ligating band spreader 38 by inserting each of the tines 42 into one of the manipulation apertures 22. Next, the physician manipulates the ligating band spreader 38 to increase the interior diameter d of the ligating band 1, and positions the ligating band 1 adjacent to the first section of tissue T1. A portion of the tissue is then drawn through the ligating band 1 (using a clamping device 40 for example), and the physician manipulates the ligating band spreader 38 to decrease the interior diameter d of the ligating band 1 until the texturing 10 engages the tissue 36.

By manipulating the ligating band spreader 38, the physician may not only position the ligating band 1 over the tissue 36, but may also subsequently wholly or partially disengage the ligating band 1 from the tissue 36 to allow the physician to reposition the ligating band 1 relative to the tissue 36. The physician may use the ligating band spreader 38 whether the ligating band 1 was initially placed over the tissue 33 using a ligating band spreader 38 or using a ligating band dispenser 32.

Figure 17:
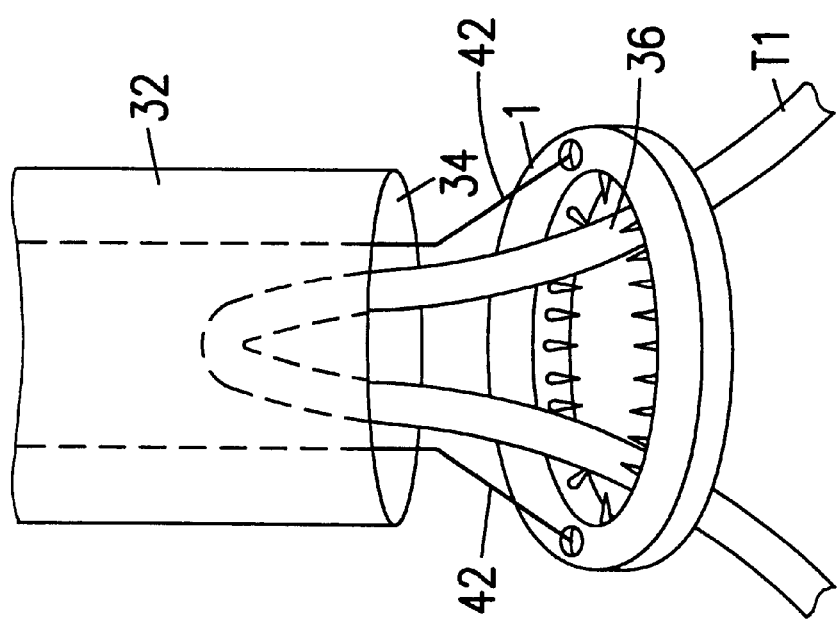
FIG. 17 shows a side view of a distal end of an alternate ligating band dispensing device specifically adapted for use with textured ligating bands.

Finally, FIG. 17 shows the distal end 50 of an alternate ligating band dispensing device including a ligating band supporting structure 52 which has a diameter which decreases from a maximum diameter at a proximal end 54 to a minimum diameter at a distal end 58. Thus, the ligating band supporting structure 52 may be formed as a portion of a cone. As shown in FIG. 17, the proximal end 54 is received within a sleeve 60 which forms an abutting surface 62 adjacent to the outer surface of the proximal end 54 so that, when a plurality of ligating bands 4 are received on the ligating band supporting structure 52, a proximal most ligating band 4 may not move proximally past the abutting surface 62. The ligating band supporting structure 52 is coupled within the distal end 50 so that the ligating band supporting structure 52 may be moved proximally relative to the abutting surface 62, for example by being screwed into the sleeve 60 by rotation about the central axis C in the direction of arrow A. Thus, as the ligating band supporting structure 52 is moved into the sleeve 60, the proximal-most ligating band 4 abuts the abutting surface 62 and pushes the more distal ligating bands 4 toward the distal end 58 until they are dispensed therefrom one-by-one. Eventually, when the distal end 58 is drawn proximally past the abutting surface 62, the proximal-most ligating band 4 is dispensed from the ligating band supporting structure 52. Thus, as the force urging the ligating bands 4 off the ligating band supporting structure 52 is applied around the entire circumference of the ligating bands 4, the increased frictional forces associated with the textured ligating bands according to the present invention may more easily be overcome.

Still other objects and advantages of the present invention will become readily apparent to those skilled in the art from the detailed description, wherein the preferred embodiment and several alternate embodiments of the invention have been shown and described. The description of the preferred embodiment is simply by way of illustration of the best mode contemplated for carrying out the invention. As will be realized, the invention is capable of other and different embodiments, and its several details are capable of modification in various respects, all without departing from the invention. Accordingly, the drawings and descriptions are to be regarded as illustrative in nature, and not as restrictive of the invention which is to be limited only by the claims appended hereto.

What is claimed is:

1. An elastic band for ligating tissue within a living body, comprising:

a ring formed of elastomeric material, the ring including an inner surface defining a lumen, and the ring including a second surface; and a plurality of projections disposed on the inner surface and the second surface, each of the projections including a substantially cylindrical stem and a substantially hemispherical cap, wherein prior to deployment the cylindrical stem and hemispherical cap of the projections on the second surface have longitudinal axes substantially orthogonal to longitudinal axes of the projections on the inner surface.

2. The elastic band according to claim 1, wherein the projections of the inner surface are arranged in a predetermined pattern so that each of the projections faces across a central opening of the ring to a space between projections formed on a corresponding opposite portion of the inner surface.

3. A method of ligating tissue within a living body, comprising:

positioning an elastic band which has been stretched to increase the size of a central opening extending therethrough adjacent to a portion of tissue to be ligated, the elastic band including a ring formed of elastomeric material, the ring including an inner surface and a second surface, the elastic band further including a plurality of projections disposed on the inner surface and the second surface, each of the projections including a substantially cylindrical stem and a substantially hemispherical cap, wherein prior to deployment the cylindrical stems and hemispherical caps of the projections on the second surface have longitudinal axes substantially orthogonal to longitudinal axes of the projections on the inner surface;

drawing a portion of tissue to be ligated through the central opening of the elastic band; and releasing the elastic band so that the size of the central opening decreases to grip the tissue received therein.

4. The method according to claim 3, wherein the projections are arranged in a predetermined pattern so that each of the projections faces across a central opening of the ring to a space between projections formed on a corresponding opposite portion of the inner surface.

5. An elastic band for ligating tissue within a living body, comprising:

a ring formed of elastomeric material, the ring including an inner tissue engaging surface, which, when in an operative position within the body, surrounds and directly contacts the tissue, and the ring including a second surface;

an interior reservoir formed within the ring, the interior reservoir sized to retain fluid; and a plurality of projections each disposed on and integrally formed with the inner surface, at least a portion of each of the plurality of projections being formed of the elastomeric material and each the projections including an injection prong.

6. A method of ligating tissue with a living body, comprising:

positioning an elastic band which has been stretched to increase the size of a central opening extending therethrough adjacent to a portion of tissue to be ligated, the elastic band including a ring formed of elastomeric material and the elastic band including an electrically conductive member extending from the inner surface to a contact point accessible from a proximal side of the elastic band, the ring including an inner tissue engaging surface which, when in an operative position within the body, surrounds and directly contacts the tissue, and the elastic band further including a plurality of projections each disposed on and integrally formed with the inner surface and each of the projections including an injection prong;

drawing a portion of tissue to be ligated through the central opening of the elastic band;

releasing the elastic band so that the size of the central opening decreases to grip the tissue received therein; and applying RF energy to the tissue through the electrically conductive member.

\* \* \* \* \*